Feb. 26, 1974 M. C. BALLAS Plant Pat. 3,497
IVY PLANT
Filed Nov. 2, 1972
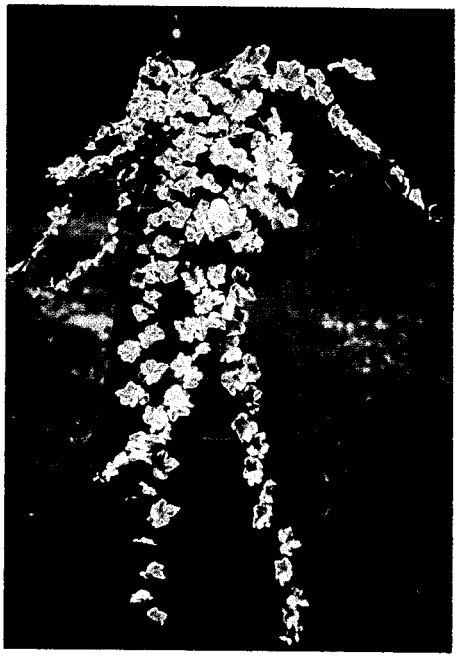
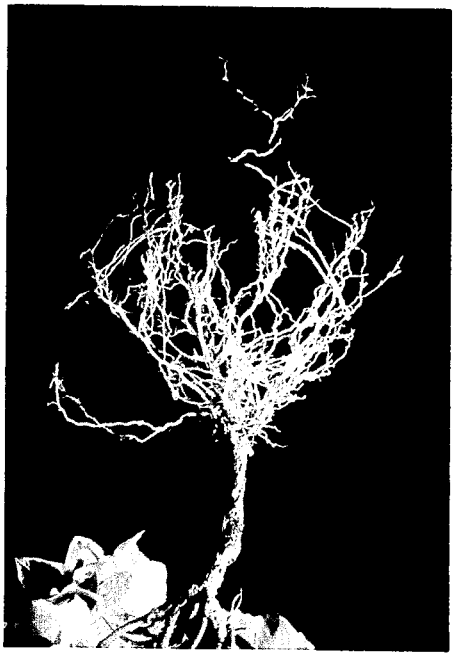
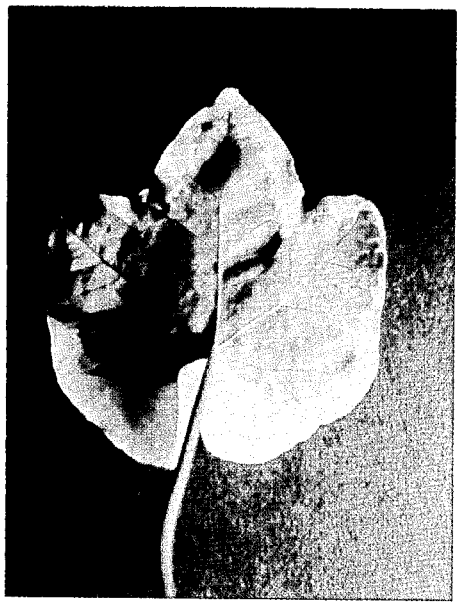
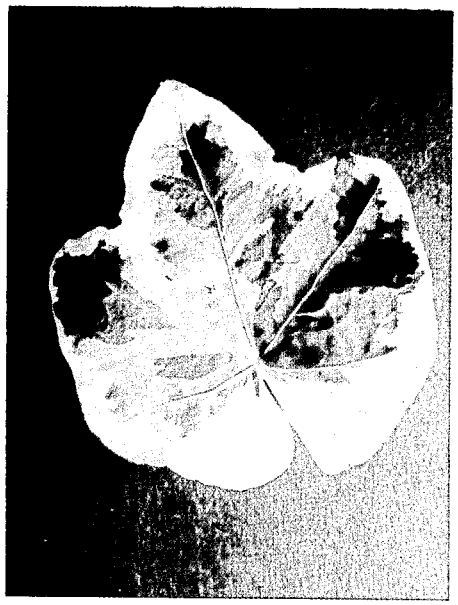

United States Patent Office

Plant Pat. 3,497
Patented Feb. 26, 1974

3,497
IVY PLANT

Milton C. Ballas, North Plainfield, N.J., assignor of a fractional part interest to Anastasia C. Ballas Filed Nov. 2, 1972, Ser. No. 303,020
Int. Cl. A01g 5/00
U.S. Cl. Plt.—67 1 Claim The present invention relates to a new and distinct variety of ivy plant which was discovered by me in my nursery as a cultivated sport or off-shoot mutation of the ivy variety known as "Curlielock" (unpatented).

At the time of my discovery, I was growing in my nursery, located at North Plainfield, N.J., some ivy plants of the variety "Curlielock" which normally bears chubby, curly leaves of solid dark green color and varying in size from ¼ inch to about 1½ inches in diameter. During my care of these plants, my attention was attracted to one particular plant which bore leaves that were an attractive and distinctive dark yellowish green color with an ivory white border. On close inspection of this particular plant, I found that it had sported at an off-shoot break that had developed on one stem thereof. I thereupon carefully preserved the sport and kept it under close observation. In due course, I asexually reproduced the sport by means of rooted cuttings, as performed by me in my nursery aforesaid.

Continued observations of the original sport and its progeny, derived as aforementioned, from the cuttings taken therefrom, showed that the 2-toned green and white leaf color variegation was established and came ture, among other distinctive features noted in the course of my observations and tests. I am accordingly convinced that my new sport is definitely a new and distinct variety of ivy plant which is distinguished from its parent variety, as well as from all other varieties of which I am aware, as particularly evidenced by the following principal characteristics which are outstanding therein:

(1) The production of vines which grow from 3 to 5 or more feet in length if not cut back, said vines being full and plush at the top and attractively cascading from the base in irregular shapes;
(2) A vigorous and rapid-growing rooting habit, and the ability to be propagated readily and easily from rooted cuttings;
(3) Distinctive and attractive leaves which are relatively round in general shape but having five lobes, said leaves being about two inches in diameter when mature and being symmetrical on both sides of the vines, with tiny clusters of small leaf off-shoots breaking at the base of each large leaf and which tend to give the vine a very compact appearance;
(4) A tendency of the leaves to curl when exposed to full sunlight; and
(5) A distinctive and attractive leaf color which sometimes is practically all yellowish white at first, but which changes as the leaves develop and mature to ivory white at the edges and moderate yellow-green over the central area, and finally to a semi-glossy dark yellowish green color with an ivory white border when fully mature.

The accompanying drawing shows a typical plant of my new ivy variety, as well as a typical root system thereof, and additionally shows the upper and under surfaces. respectively, of typical leaf specimens on a larger scale than in the other views, all as depicted in color as nearly true as it is reasonably possible to make the same in a color illustration of this character.

The following is a detailed description of my new ivy variety, with color terminology in accordance with Nickerson's Color Fan, published by Munsell Color Co., Inc., of Baltimore, Md., except where general color terms of ordinary dictionary significance are obvious:

Parentage: Sport of "Curlielock" Ivy.
Propagation: Holds its distinguishing characteristics through succeeding propagations by rooted cuttings.
Locality where grown and observed: North Plainfield, N.J.

Plant:

*Rooting habit.*—Vigorous rapid growing.

*Vine.*—Full and plush at top, with each vine cascading in irregular shapes from the base; irregular lengths, but usually will attain lengths of from 3 to 5 feet if not cut back. Color—Reddish brown.

Leaves:

*Petiole.*—From about ¼ inch to about 1¾ inches long; from about 1/32 inch to about 1/16 inch in diameter.

*Internodes.*—From about ¾ to about 1¼ inches, with tiny clusters of small leaf off-shoot breaks growing from base of each large leaf and giving the vine a very compact appearance.

*Shape.*—Almost round, but 5-lobed; lobes rounded at edges except at tip of leaf which is somewhat more pointed at apex but not substantially longer than adjacent lobes; leaves have a tendency to curl when exposed to full sunlight.

*Veins.*—Fairly prominent; 5 principal veins. Color —From greenish white to moderately reddish brown as leaves age.

*Color of leaves.*—Irregular 2-toned green and white variegation on both surfaces. When young—Sometimes entirely yellowish white at first, and then changing to Light Yellow Green, Color No. 7.5 GY 9/4. When mature—Irregular central area ranging from dull grayish green to from Strong Yellowish Green, Color No. 2.5 G 5/9 to near Dark Yellowish Green, Color No. 10 GY 4/5, with irregular ivory white border surrounding entire leaf edge; green colors sometimes semi-glossy in some areas on upper surface, and more uniformly grayish green on under surface.

I claim:

1. A new and distinct variety of ivy plant, substantially as herein shown and described, characterized particularly as to novelty by the unique combination of the production of vines which grow from 3 to 5 or more feet in length if not cut back, said vines being full and plush at the top and attractively cascading from the base in irregular shapes, a vigorous and rapid-growing rooting habit, and the ability to be propagated readily and easily from rooted cuttings, distinctive and attractive leaves which are relatively round in general shape but having five lobes, said leaves being about two inches in diameter when mature and being symmetrical on both sides of the vines, with tiny clusters of small leaf off-shoots breaking at the base of each large leaf and which tend to give the vine a very compact appearance, a tendency of the leaves to curl when exposed to full sunlight, and a distinctive and attractive leaf color which sometimes is practically all yellowish white at first, but which changes as the leaves develop and mature to ivory white at the edges and moderate yellow green over the central area, and finally to a semi-glossy dark yellowish green color with an ivory white border when fully mature.

No references cited.

ROBERT E. BAGWILL, Primary Examiner